United States Patent [19]

Rogozinski

[11] Patent Number: 5,007,909
[45] Date of Patent: Apr. 16, 1991

[54] APPARATUS FOR INTERNALLY FIXING THE SPINE

[76] Inventor: Chaim Rogozinski, 4453 Forest Dr. South, Jacksonville, Fla.

[21] Appl. No.: 928,647

[22] Filed: Nov. 5, 1986

[51] Int. Cl.⁵ .............................................. A61F 5/00
[52] U.S. Cl. ...................................................... 606/61
[58] Field of Search ............... 623/17; 128/92 YM, 69; 606/61

[56] References Cited

U.S. PATENT DOCUMENTS

| | | | |
|---|---|---|---|
| 2,502,902 | 4/1950 | Tofflemire | 128/92 R |
| 3,242,922 | 3/1966 | Thomas | 128/92 R |
| 4,274,401 | 6/1981 | Miskew | 128/69 |
| 4,411,259 | 10/1983 | Drummond | 128/69 |
| 4,422,451 | 12/1983 | Kalamchi | 128/69 |
| 4,448,191 | 5/1984 | Rodnyansky et al. | 128/69 |
| 4,567,884 | 2/1986 | Edwards | 128/69 |
| 4,611,582 | 9/1986 | Duff | 128/69 |

FOREIGN PATENT DOCUMENTS

| | | | |
|---|---|---|---|
| 3032237 | 3/1982 | Fed. Rep. of Germany | 128/69 |
| 441932 | 12/1974 | U.S.S.R. | 128/69 |
| 654251 | 3/1979 | U.S.S.R. | 128/69 |
| 1063404 | 12/1983 | U.S.S.R. | 128/69 |

*Primary Examiner*—Clifford D. Crowder
*Attorney, Agent, or Firm*—Edward S. Irons

[57] ABSTRACT

A method of correcting spinal deformities and a spinal fixation system for use in the method. After surgically exposing the spine posteriorly, a series of clamps are affixed to the laminae of the vertebrae. Beginning at either end of the line of clamps, a rod attachment device is attached to each affixed clamp. Again, beginning at either end of the line, a rod is inserted into the rod attachment devices. Compression or distraction is then applied to the spine between successive vertebrae proceeding from one clamp to the next until all clamps are secured to the rod.

5 Claims, 3 Drawing Sheets

APPARATUS FOR INTERNALLY FIXING THE SPINE

This application on is a continuation of application Ser. No. 784,124 filed Oct. 4, 1985, now abandoned.

BACKGROUND OF THE INVENTION

The present invention relates to an apparatus and method for correcting spinal deformities such as scoliosis and kyphosis, and for internal fixation of the spine.

Spinal deformities of interest here are chiefly characterized by geometric deviation of the spinal column from that of the normal configuration as well as spinal instabilities. For example, scoliosis is a lateral deviation of the spinal column from the essentially normal straight line configuration as viewed from the ventral or dorsal of the spinal column. When these abnormal spinal curvatures exceed certain limits correction by surgical treatment must be considered. The surgical treatment for such conditions is known as arthrodesis and involves both the correction of the curvature of the spine in the region of deviation to the maximum possible extent and also the fusion by autogenous bone grafts of the vertebrae in the region of abnormal curvature. Correction of the spinal configuration can be attempted prior to surgical treatment by continuous traction of the spine or by corrective plaster casts. However, a corrected and fixed configuration of the vertebrae must be maintained during the period in which vertebrae are being fused so that the deformity is corrected by the final fusion.

A known surgical technique for maintaining corrected positioning of vertebrae during the fusion process involves the attachment, by hooks, of rods to the spine. The rods are used to apply forces to straighten the spine and to maintain the corrected configuration until the vertebrae are fused. Hooks and a threaded rod are attached to the dorsal or posterior elements of vertebrae of the spine on the convex side of the deformity such that compression can be applied to the vertebrae and thus correct the spinal configuration. Hooks with a second rod are also attached to the laminae on the concave side of the deformity to provide distraction by the reverse application of force as is provided by the compression system of hooks and threaded rod on the convex side of the deformity. Such systems of hooks and rods is known as Harrington instrumentation. Harrington type instrumentation is disclosed in U.S. Pat. Nos. 4,269,178; 4,274,401; 4,361,141; 4,369,769; 4,369,770; 4,382,438; 4,386,603; 4,404,967; 4,409,968; 4,411,259; and, 4,422,451.

Another known surgical technique for maintaining corrected positioning of vertebrae during arthrodesis involves attachment by screws or staples to the ventral or anterior of vertebrae on the convex side of the deformity, and the interconnection of the stapled vertebrae by passing a cable, such as braided titanium wire, through holes in the heads of the screws affixing the staples to the vertebrae. Then starting at one end, pairs of stapled vertebrae are compressed by applying tension to the cable to straighten the curve. Compression between vertebrae is maintained by crimping the screwheads into the cable. This system of staples, screws, and cable is known as Dwyer instrumentation.

Though the Harrington and Dwyer instrumentation systems have predominantly been independently used for treatment of deformed spines, they have been also used in combination for the treatment of patients with painful adult idiopathic scoliosis. First the Dwyer procedure was used in this combination treatment, and later the Harrington procedure was performed. This combined use of Harrington and Dwyer instrumentation on patients is outlined in more detail in the article "Combined Dwyer and Harrington Instrumentation and Fusion in the Treatment of Selected Patients With Painful Adult Idiopathic Scoliosis", Spring, June, 1978, pp. 135-141.

A third known surgical technique for maintaining corrected positioning of vertebrae during the fusion process involves the attachment, by wires, of rods to the spine. The rods are used for support to straighten the spine, and also to maintain the corrected configuration until the vertebrae are fused. To attach the rods to the spine, wires are passed about the laminae on each of the two posterior sides of each vertebra to which the rods are to be attached. Then beginning on the convex side of the deformation, a first rod is positioned adjacent the spinous processes of the vertebrae at one end of the line of vertebrae to be attached, and the wires on that side of the vertibrae are twisted about the rod to attach it to the vertebrae. Progressing along the line of vertebrae, the spinal column is levered against the rod and wires mounted about each vertebra are twisted about the rod to maintain the spinous processes on the convex side of the deformation adjacent the rod. This attachment of vertebrae to the rod corrects the spinal deformity. A second rod to augment the strength of the instrumentation is then placed adjacent the other side of the spinous processes from the first rod, and the wires mounted about the laminae on the side of the vertebrae adjacent the second rod are twisted about the second rod to maintain it in a support position against the vertebrae. This system of rods and wires is known as Luque spinal instrumentation.

SUMMARY OF INVENTION

Substantial disadvantages are associated with both the Harrington and Dwyer type instrumentation. For the Harrington type instrumentation the disadvantages include the inherent difficulty associated with simultaneously attempting to seat the hooks mounted on the compression or distraction rods to transverse processes of the vertebrae to be instrumented. Frequently, the hooks unseat while an adjacent level is being instrumented. Attempts to overcome this particular problem have included the use of slotted hooks which are seated on processes of vertebrae prior to the attachment of a rod. However, even this approach involves awkward simultaneous manipulation of multiple components, because the constraining parameter is the rod to which all of the hooks must be affixed while also engaging various vertebrae. It is the rod and the utilization of hooks which are attached to vertebrae that causes major difficulties in the application of Harrington instrumentation to the spinal column. As for the Dwyer type instrumentation, here major problems arise due to the inherent difficulties associated with orthopedic surgeons having to operate on the front of the spine. Further the anterior portion of vertebrae is soft, and, therefore, screws can be stripped from vertebrae. Exacerbating this situation is the unavoidable uncertainty of assuring proper compression of screw heads into the cable, i.e. insufficient compression could permit slippage of the cable, or excessive compression could cut the cable. Finally, for the Luque spinal instrumentation there is the risk of the wires breaking. Due to the tension generated by this instrumentation these wires do frequently break. Such breakage of course significantly increases the risk of neurotogic injury. The present invention overcomes these and other disadvantages.

The present invention utilizes a clamp system, i.e. two hook structures assembled in a clamping fashion using a nut and bolt. The hook structures are so dimensioned and the nuts and bolts are so mounted that each clamp can be firmly attached to the laminae of vertebrae. Each clamp additionally has a transverse hole which can accept an adjustable rod clamp. A bolt and nut firmly affix an adjustable rod clamp to each clamp. After clamps are firmly attached to the laminae of vertebrae on the tension or compression, or both sides of the abnormal deformation, a rod is passed through the holes in each adjustable rod clamp. Then starting at the caudal end of the line of clamped vertebrae, pairs of clamped vertebrae are compressed or distracted by applying tension or distraction to the adjustable rod clamp which straightens, derotates and effectively immobilizes the deformed section of the spinal column. The applied compression or distraction between clamped vertebrae can be maintained by tightening adjustable rod clamp nuts onto the adjustable rod clamp bolts.

The system of clamps, rods and adjustable rod clamps of the present invention can also be used to fuse lumbar vertebrae to the sacrum S1. For example, by affixing a first clamp on one side of the laminae and a second clamp on the other side of the laminae of the lumbar vertebra L4, and then passing rods through the adjustable rod clamp holes in the affixed clamps the rods can be directed at the pelvis in the region of the posterior superior iliac spine of the ipsilateral side. The rods can then be passed through holes which are drilled through the pelvis. The rods are anchored to the pelvis by washers on both cortecies. The washers increase the surface area of the rods anchored to the pelvis. Now both the first and second rods can be used to apply tension between the pelvis and the lumbar vertebra L4 so that L5 can be properly configured and fixed with respect to the sacrum S1 for fusion of the bones. This tension in both rods is maintained by affixing the respective rods to the first and second adjustable rod clamps.

Arthrodesis can be accomplished using the clamps and rods of the present invention at the cervical, thoracic, lumbar or sacral regions of the spinal column. Further, this invention can be used for treatment of vertebral fractures at the cervical, thoracic or lumbar regions of the spinal column.

Unlike previous instrumentation for accomplishing arthrodesis, such as the Harrington and Dwyer types, the present invention allows ample access to the intervertebral area for decortication associated with autogenous bone grafts. Additionally, the clamps and rods of the present invention permits locking of facets necessary for fusion.

BRIEF DESCRIPTION FROM THE DRAWINGS

The features and objects of the invention, as well as others, will be apparent to those skilled in art by referring to the accompanying drawings in which.

DETAILED DESCRIPTION OF THE INVENTION

Figure 1:
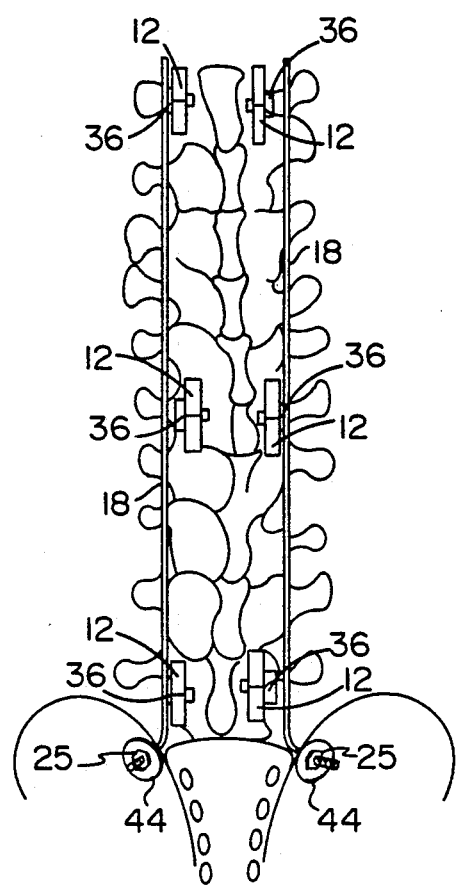
FIG. 1 is an illustration of the use of the clamps and rods of the present invention engaging a spinal column and pelvis.

The drawings will now be referred to for showing the invention. Throughout the various figures corresponding components are designated by the same reference numerals.

Figure 2:
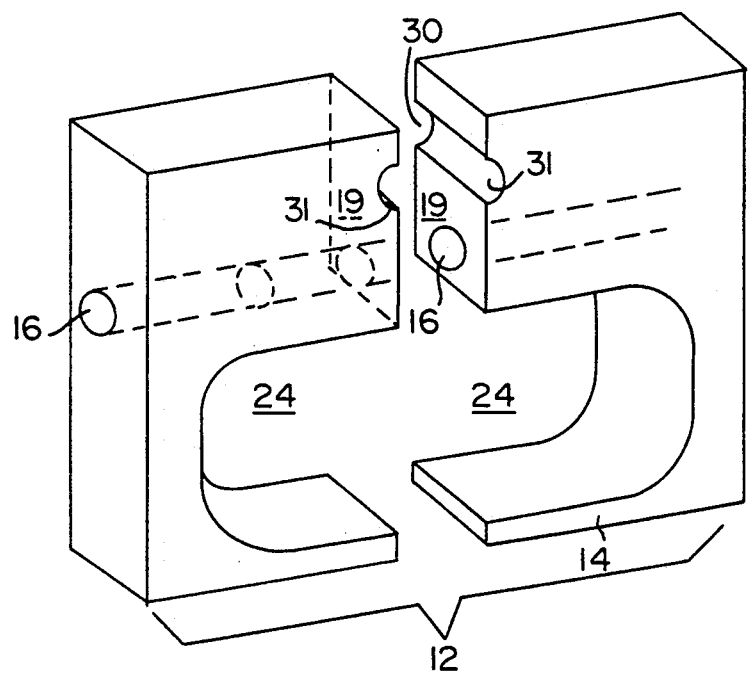
FIG. 2 is a perspective view of a clamp of the present invention.
Figure 4:
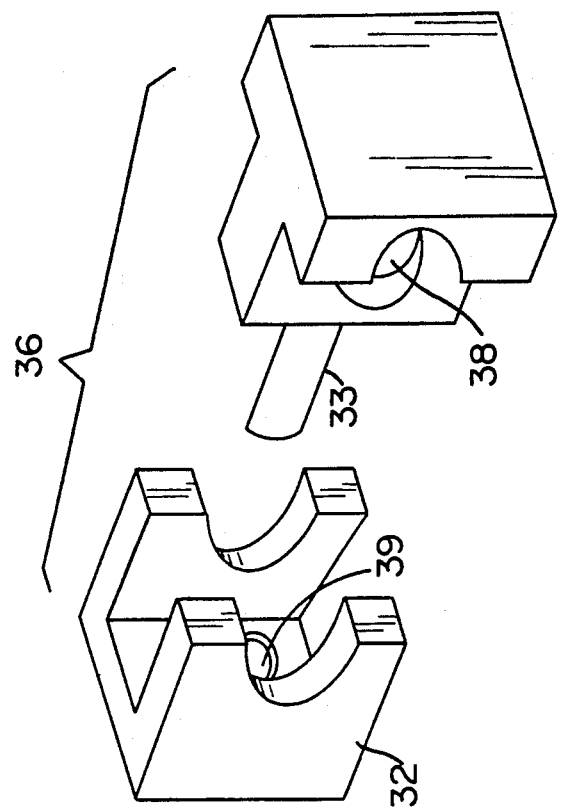
FIG. 4 is an exploded view of an adjustable rod clamp.
Figure 3:
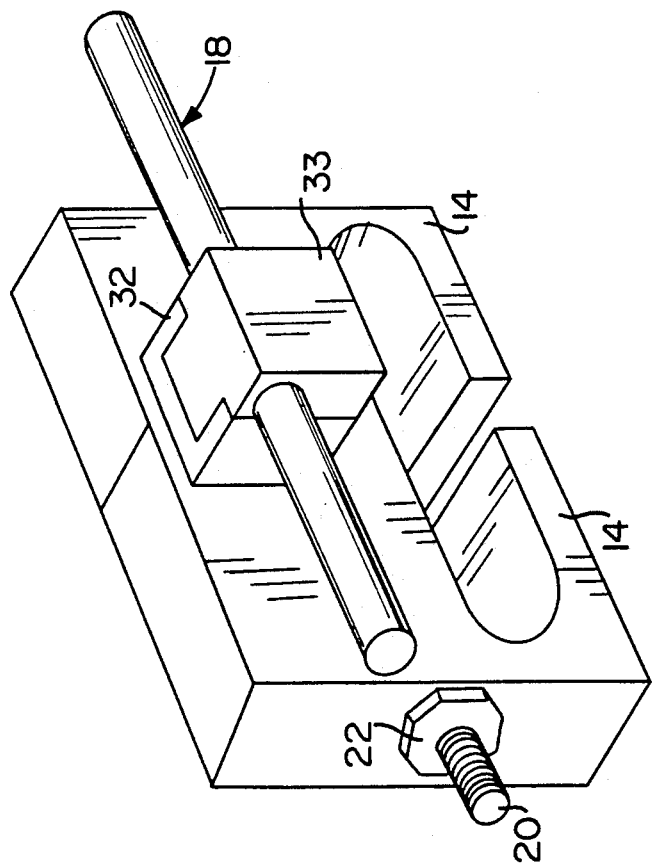
FIG. 3 is a perspective view of an assembly including a rod attached to a clamp, via an adjustable rod clamp.
Figure 5:
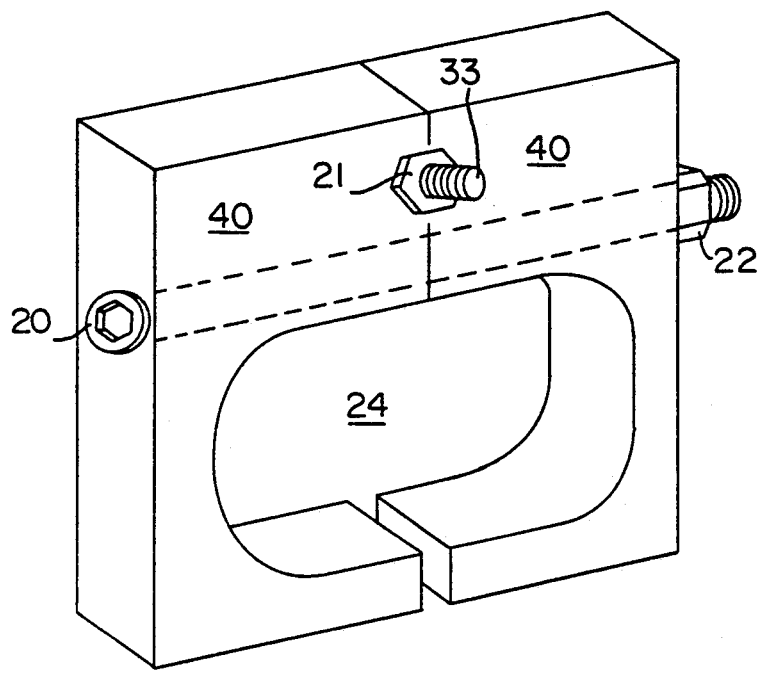
FIG. 5 is a perspective view of an adjustable rod clamp affixed to a clamp.
Figure 6:
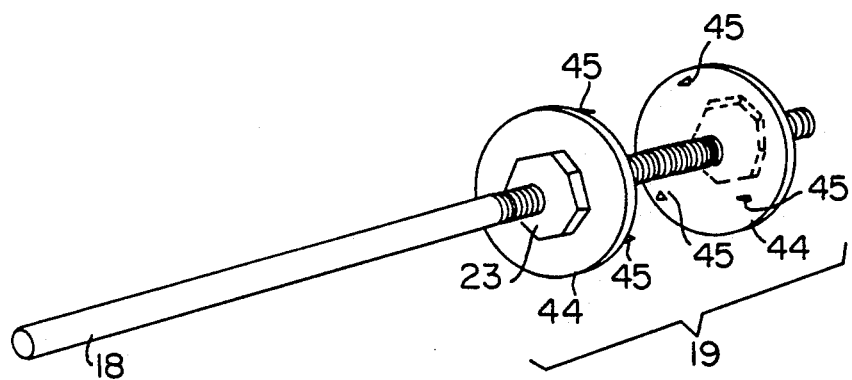
FIG. 6 is a perspective view of the pelvic attachment system showing a threaded rod with two spiked washers and nuts; and, FIG. 7 is an illustration of the use of rods and clamps as well as nuts and washers of the present invention engaging the lower spine including the pelvis.

Clamps, as generally designated by numeral 12 (see FIG. 2), are an essential portion of the present invention. The clamps 12 are assembled from two opposing essentially identically dimensioned hook structures 14. These hook structures 14 can be fabricated from stainless steel or other suitable material. Included on one side of both hook structures 14 are lateral holes 16. When two hook structures 14 are positioned against each other at the surfaces 19 adjacent lateral holes 16 a second hole 30 is formed from two concave surfaces 31 in the two hook structures 14. The two hook structures 14 are assembled together via a bolt 20 positioned in lateral holes 16 and secured with a nut 22. The second hole 30 is essentially transverse to the lateral hole 16. Rotation of the hook structures 14 with respect to each other about the connecting bolt 20 is inhibited by a transverse eye bolt 33 (see FIGS. 3 and 4) which is part of an adjustable rod clamp 36. The adjustable rod clamp 36 is secured to clamp 12 by the transverse eye bolt 33 and nut 21. Therefore, when the surfaces 19 adjacent holes 16 are brought into contact and the transverse eye bolt 33 is inserted, rotation of the hook structures 14 with respect to each other is prevented.

The dimensions of the laminae jaws 24 of the hook structures 14 are selected so as to form clamp 12 in an arrangement which can be firmly seated against the lamina of a vertebra. Thus the clamp 12 and the attached vertebra form a rigid, essentially unitary structure. The lamina of the vertebra, which are the strongest portions of a vertabra, provide a convenient and sturdy structure to which the clamps 12 can be affixed. Therefore, by fixedly mounting clamps 12 to the laminae of vertebrae, the holes 30 in clamp 12 provide sturdy attachment sites for adjustable rod clamps 36, to which a rod 18 can be affixed to interconnect the vertebrae on which clamps 12 have been mounted.

Using the present invention, the formation of the spine can be corrected by fixedly attaching the clamps 12 to the laminae of vertebrae which when compressed on the tension side of a deformation and distracted on the compression side of a deformation realigns the spinal column into a correct configuration. To provide and maintain the desired alignment of the vertebrae, a rod 18 is passed through holes 38 in the adjustable rod clamps 36 mounted on vertebrae. The adjustable rod clamps 36 are formed by eye bolts 33 and jaws 32 (see FIG. 4). The desired alignment is achieved by beginning at either the caudal or rostral end of a line of clamped vertebrae. Pairs of clamped vertebrae are compressed or distracted by applying compression or distraction to consecutive adjustable rod clamps 36. A retentron system is provided at each adjustable rod clamp 36 to prevent movement of rod 18 with respect to the next adjustable rod clamp 36 after tension or compression on the rod 18 has been properly adjusted between clamped vertebrae. The retention system at each adjustable rod clamp 36 is provided by tightening nut 21 on to bolt 33.

As nut 21 is tightened a jaw surface 40, compresses rod 18 against the hole 38 in eye bolt 33. The compression or distraction between consecutive clamps 12 is adjusted and then the nuts 21 are tightened to maintain the proper distance between consecutive clamps 12.

After clamps 12 have been affixed to vertebrae, and rod 18 has been adjusted to apply compression or distraction or both between vertebrae so the deformity of the spinal column has been corrected to the greatest extent feasible, and the rod 18 has been restrained with respect to each affixed clamp 12, the posterior arches of the vertebra can be fused by decortication and addition of autologus spongy bone or bone bank bone so that vertebral arthrodesis can be achieved.

Figure 7:
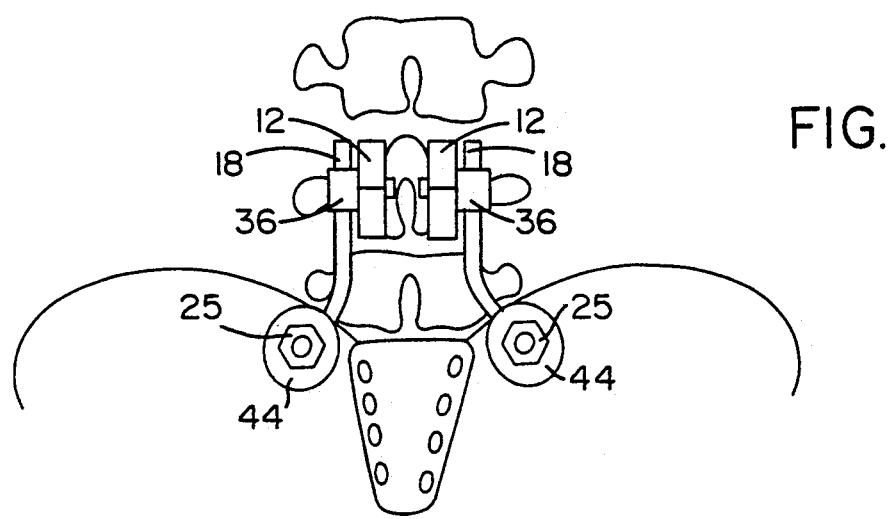

In addition to being able to use clamps 12 and the rod 18 at the thoracic and lumbar regions of the spinal column, the present invention can also be used to fuse the sacrum S-1 bone to lumbar vertabra L-5. An example of this use of the present invention is shown in FIG. 7. Here the clamps 12 are fixedly attached on both sides of the posterior of lumbar vertebra L-4 to the lamina, and the rods 18 are passed through the adjustable rod clamps 36. The distal ends 19 of the rods 18 are threaded. The rods 18 are bent to the proper angle as determined by each individual pelvis. Prior to passing each rod 18 through holes drilled in the pelvic wall, a first nut 23 and a first washer 44 are positioned on the threaded ends 19 of rods 18. After each rod 18 has been passed through a hole drilled in the pelvic wall a second washer 44 and a second nut 25 are positioned onto the threaded end 19 of the rods 18. At this point the proper tension or distraction between clamps 12 is adjusted and nuts 21 are tightened on to eye bolts 33. Compression is then applied across the L5-S1 fusion site by tightening nut 25 to rods 18 which is on the outer pelvic wall. Purchase on inner and outer pelvic walls between the adjacent washers number 44 is then obtained. Washers 44 have three small spikes 45 in order to avoid translation of the washer on either the inner or outer pelvic wall.

The above discussion and related illustrations of the present invention are directed primarily to preferred embodiments and practices of the invention. However, it is believed that numerous changes and modifications in the actual implementation of the concepts described herein will be apparent to those skilled in the art, it is contemplated that such changes and modifications may be made without departing from the scope of the invention as defined by the following claims.

What is claimed is:

1. A method for correcting deformaties or instabilities of the spine by posterior surgical procedures, which method comprises:

surgically exposing the spine posteriorly;
affixing clamps onto the laminae of vertebrae;
beginning at either end of the line of affixed clamps attaching rod attachment means to each of said clamps; and
beginning at either end of said line of affixed clamps inserting a rod into said rod attachment means;
compression or distraction being applied to the spine between a first clamp and a second clamp in the line of clamped vertebrae by fixedly securing said rod to said first clamp and compressing or distracting said second clamp with respect to said first clamp and fixedly securing said rod to said second clamp, proceeding from the secured second clamp to the next clamp in the line of clamped vertebrae and compressing or distracting the next clamp with respect to said second clamp and fixedly securing said rod to said next clamp until all clamps are secured to said rod.

2. A method for correcting deformities or instabilities of the spine by a posterior surgical procedure, which method comprises:

surgically exposing the spine posteriorly;
affixing a first clamp with a first rod attachment means onto the lamina of a vertebra on a first side of the spinous process;
affixing a second clamp with a second rod attachment means onto the lamina of a vertebra on the second side of the spinous process;
attaching a first rod to said first rod attachment means directing said first rod along the longitudinal axis of the spine so that said first rod can be affixed to the posterior superior iliac spine and applying lamina compression to the spine by the tension exerted on said first rod between said posterior superior iliac spine where said first rod is affixed and said first clamp where said first rod is affixed to said first rod attachment means;
attaching a second rod to said second rod attachment means directing said second rod along the longitudinal axis of the spine so that said second rod can be affixed to the posterior superior iliac spine and applying laminar compression to the spine by the tension exerted on said second rod between said posterior iliac spine where said second rod is affixed and said second clamp where said second rod is affixed to said second rod attachment means.

3. A surgically implanted spinal fixation support system comprising at least one rod and a plurality of clamping means, each clamping means having jaws sized for fixedly attaching said clamping means to the laminae of vertebrae, each of said clamping means having means for adjustably attaching rod attachment means to said clamping means along the length of said rod means, and means for fixedly attaching said rod to said rod attachment means.

4. The spinal fixation support system of claim 3 wherein each of said clamping means consists of two opposing hook structures retained by a bolt and nut so that as said bolt and nut are tightened said hook structures are rigidly affixed to a lamina of a vertebra.

5. The spinal fixation support system of claim 3 wherein each of said rod attachment means includes (a) a transverse hole large enough in size so as to enable said rod to pass freely through said hole; and, (b) a clamping means for fixedly attaching said rod to said rod attachment means.

* * * * *